United States Patent
Graf et al.

(10) Patent No.: US 10,444,380 B2
(45) Date of Patent: Oct. 15, 2019

(54) DEVICE FOR THE SPATIALLY RESOLVED MEASUREMENT OF PHOTONS

(71) Applicant: Siemens Healthcare GmbH, Erlangen (DE)

(72) Inventors: Alexander Graf, Forchheim (DE); Gerald Hauke, Nuremberg (DE); Thomas Hilderscheid, Altdorf (DE); Klaus Windsheimer, Spalt (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 104 days.

(21) Appl. No.: 15/703,106

(22) Filed: Sep. 13, 2017

(65) Prior Publication Data
US 2018/0081070 A1    Mar. 22, 2018

(30) Foreign Application Priority Data
Sep. 20, 2016  (DE) .......................... 10 2016 217 993

(51) Int. Cl.
*G01T 1/208* (2006.01)
*G01T 1/24* (2006.01)
(Continued)

(52) U.S. Cl.
CPC .............. *G01T 1/208* (2013.01); *A61B 6/032* (2013.01); *G01N 23/046* (2013.01); *G01T 1/175* (2013.01);
(Continued)

(58) Field of Classification Search
CPC ..... G01T 1/208; G01T 1/2006; G01T 1/2018; G01T 1/247; G01T 1/175; H04N 5/32; G01N 23/046; A61B 6/032
See application file for complete search history.

(56) References Cited

U.S. PATENT DOCUMENTS

2006/0231767 A1*  10/2006  Danzer ................. G01T 1/2985
                                                  250/370.11
2010/0172466 A1    7/2010  Herrmann et al.
(Continued)

FOREIGN PATENT DOCUMENTS

CN          1865955 A     11/2006
CN        101501527 A      8/2009
(Continued)

OTHER PUBLICATIONS

Tietze, Ulrich et al.: "Halbleiter-Schaltungstechnik". 6. Aufl. Berlin [u.a.]: Springer, 1983. Titelseite+ pp. 519-523.—ISBN 3-540-12488-8; 1983.
(Continued)

*Primary Examiner* — David P Porta
*Assistant Examiner* — Jeremy S Valentiner
(74) *Attorney, Agent, or Firm* — Harness, Dickey & Pierce, P.L.C.

(57) ABSTRACT

A device is for the spatially resolved measurement of photons, in particular x-ray photons. In an embodiment, the device includes a first plurality of photoelectric converters, a second plurality of current measuring apparatuses and a third plurality of voltage conditioners. Each current measuring apparatus is electrically connected to at least one photoelectric converter; each voltage conditioner is electrically connected to at least one current measuring apparatus; and each photoelectric converter is configured to generate a photocurrent from an incident photon. Each voltage conditioner is connectable to a supply bar, configured to provide a supply voltage. The voltage conditioner is configured to down-convert the supply voltage to an operating voltage of a current measuring apparatus. Each current measuring apparatus is configured to measure a photocurrent under operating voltage when this is generated in a photoelectric converter, electrically connected to the respective current measuring apparatus.

17 Claims, 2 Drawing Sheets

(51) Int. Cl.
*A61B 6/03* (2006.01)
*G01N 23/046* (2018.01)
*G01T 1/20* (2006.01)
*G01T 1/175* (2006.01)

(52) U.S. Cl.
CPC .......... *G01T 1/2006* (2013.01); *G01T 1/2018* (2013.01); *G01T 1/247* (2013.01)

(56) References Cited

U.S. PATENT DOCUMENTS

| | | |
|---|---|---|
| 2012/0326049 A1 | 12/2012 | Hannemann et al. |
| 2013/0221228 A1 | 8/2013 | Kawaguchi |
| 2015/0198724 A1* | 7/2015 | Graf .................. G01T 1/175 378/114 |
| 2015/0212215 A1* | 7/2015 | Goderer ................ G01T 1/24 378/19 |
| 2017/0025890 A1 | 1/2017 | Splinter et al. |

FOREIGN PATENT DOCUMENTS

| | | |
|---|---|---|
| CN | 101545810 B | 5/2012 |
| CN | 102841367 A | 12/2012 |
| CN | 104771185 A | 7/2015 |
| CN | 105794080 A | 7/2016 |
| DE | 102014200526 A1 | 7/2015 |

OTHER PUBLICATIONS

Chinese Office Action and English translation thereof dated May 31, 2019.

* cited by examiner

DEVICE FOR THE SPATIALLY RESOLVED MEASUREMENT OF PHOTONS

PRIORITY STATEMENT

The present application hereby claims priority under 35 U.S.C. § 119 to German patent application number DE 102016217993.4 filed Sep. 20, 2016, the entire contents of which are hereby incorporated herein by reference.

FIELD

At least one embodiment of the invention generally relates to a device for the spatially resolved measurement of photons, in particular x-ray photons, comprising: a first plurality of photoelectric converters and a second plurality of current measuring apparatuses, wherein each current measuring apparatus is electrically connected to at least one photoelectric converter, wherein each photoelectric converter is configured to generate a photocurrent from an incident photon, and wherein each current measuring apparatus is configured to measure a photocurrent under operating voltage, when this is generated in a photoelectric converter which is electrically connected to the respective current measuring apparatus.

BACKGROUND

The intensity of an x-ray which is absorbed and/or scattered by a body region of a patient to be examined is measured in a computed tomograph (CT) in various individual image recordings and a three-dimensional volume model of the body region to be examined is subsequently produced from the individual image recordings. To record the individual images, an x-ray detector used for this purpose in the CT in most cases has a multitude of detector elements which generate the individual image pixels of a recording.

On account of the comparatively high energy of the x-ray photons to be detected, the high demands regarding the resolution to be achieved and the particular structural aspects especially with regard to compact design in a CT, for detection purposes the individual high-energy x-ray photons are converted by means of a scintillator by collisions in each case into a multitude of lower energy photons, for which now, on account of the lower energy, a spatially resolved detection is significantly easier within the scope of the mentioned restrictions. For this purpose the lower-energy photons are detected by means of photodiodes, and the photocurrents generated in the individual detector pixels are in each case measured by a current measuring apparatus, for instance an ASIC.

To measure the in most cases comparatively low currents which are generated in the photodiode pixels, ASICs of this type typically require one or a number of supply voltages, which results in a disadvantageously high total power consumption across the entire detector during operation due to the measurement of the photocurrents. Furthermore, direct voltages which are as stable as possible are desirable as supply voltages, as a result of which on account of the particular aspects of a CT, the emerging alternating voltage portions are complicated to filter when conditioning the supply voltages. On this account the typical procedure involves providing approximately the desired operating voltage of the ASICs from a high supply voltage by means of one or a number of direct voltage converters in a unit for voltage conditioning and in the process suppressing the alternating voltage portions in the unit on the output side by means of a corresponding filter. The individual ASICs are supplied with voltage in each case by the unit, wherein the voltage can be regulated to the correct operating voltage of an ASIC by the linear regulator in each case.

For this purpose due to the current load of the ASICs the output voltages of the unit must however be conducted in each case to the linear regulators by means of a high-capacity cable. The power loss is also high with the known solution.

SUMMARY

At least one embodiment of the invention specifies a device for the spatially resolved measurement of photons, which enables as compact a design as possible and has as simple and stable a voltage supply as possible with a low power loss during operation.

At least one embodiment of the invention is directed to a device for the spatially resolved measurement of photons, in particular x-ray photons, comprising: a first plurality of photoelectric converters, a second plurality of current measuring apparatuses, a third plurality of voltage conditioners, wherein each current measuring apparatus is electrically connected to at least one photoelectric converter, wherein each voltage conditioner is electrically connected to at least one current measuring apparatus, wherein each photoelectric converter is configured to generate a photocurrent from an incident photon, wherein each voltage conditioner can be connected to a supply bar which is configured to provide a supply voltage and wherein the voltage conditioner is configured to down-convert the supply voltage to an operating voltage of a current measuring apparatus, and wherein each current measuring apparatus is configured to measure a photocurrent under operating voltage when this is generated in a photoelectric converter electrically connected to the respective current measuring apparatus.

At least one embodiment of the invention is directed to an x-ray detector, which comprises an apparatus as described above in at least one embodiment, and a CT with at least one such x-ray detector. The advantages cited for the embodiments of the apparatus and its developments can be applied analogously here to embodiments of the x-ray detector and the CT. In particular in a CT, on account of the technical properties of the rotating assembly, one of the core problems is namely to achieve, with limited available space, as effective a spatially resolved measurement of x-ray photons as possible, which is to have a low power loss and a stable voltage supply.

BRIEF DESCRIPTION OF THE DRAWINGS

An example embodiment of the invention is explained in more detail below with reference to a drawing. Shown schematically in each case here are.

Parts and variables which correspond to one another are provided with the same reference numerals in all the figures.

DETAILED DESCRIPTION OF THE EXAMPLE EMBODIMENTS

Figure 1:
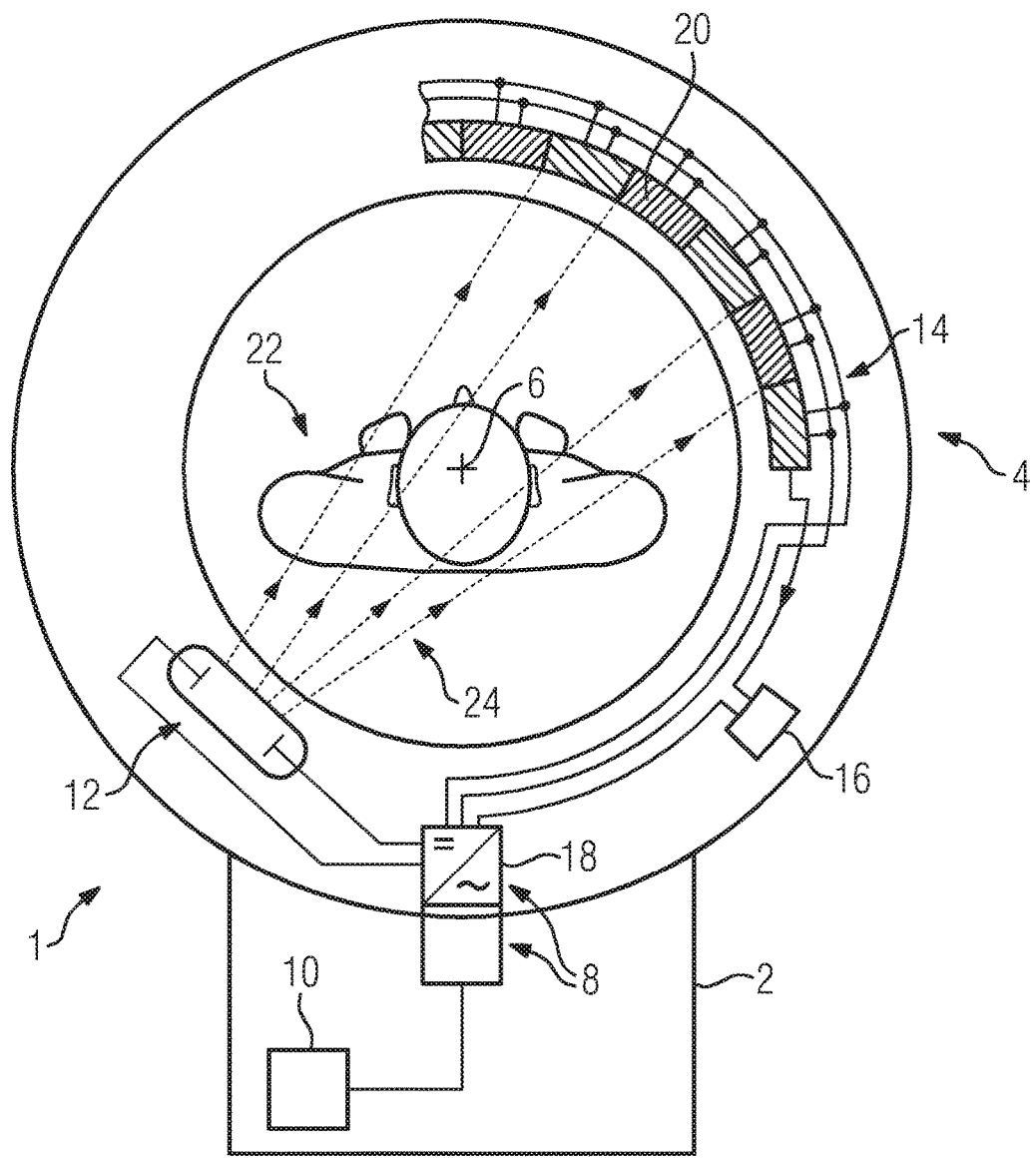
FIG. 1 a cross-sectional view of a CT with an x-ray detector.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects.

Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention is directed to a device for the spatially resolved measurement of photons, in particular x-ray photons, comprising: a first plurality of photoelectric converters, a second plurality of current measuring apparatuses, a third plurality of voltage conditioners, wherein each current measuring apparatus is electrically connected to at least one photoelectric converter, wherein each voltage conditioner is electrically connected to at least one current measuring apparatus, wherein each photoelectric converter is configured to generate a photocurrent from an incident photon, wherein each voltage conditioner can be connected to a supply bar which is configured to provide a supply voltage and wherein the voltage conditioner is configured to down-convert the supply voltage to an operating voltage of a current measuring apparatus, and wherein each current measuring apparatus is configured to measure a photocurrent under operating voltage when this is generated in a photoelectric converter electrically connected to the respective current measuring apparatus.

Advantageous and in part separately considered inventive embodiments are the subject matter of the claims and of the description which follows.

Here an electrical connection is to comprise a connection which enables a current flow and/or a voltage transmission from one part via the connection to the other part. The voltage conditioners preferably comprise in each case a corresponding terminal for the voltage supply with the supply voltage.

The first plurality of photoelectric converters is preferably arranged in a cover of a surface piece, in particular a grating or a grid structure. The supply voltage is preferably provided by a direct voltage. An operating voltage of a current measuring apparatus is understood to mean the voltage which is to be applied to the current measuring apparatus, so that this reliably generates a corresponding measuring result in the presence of an input current. Such an operating voltage of a current measuring apparatus is preferably provided by a direct voltage.

Here the use of the voltage conditioners for supplying the current measuring apparatuses with their operating voltage is preferably such that a voltage conditioner in each case only supplies one individual current measuring apparatus or a small group of current measuring apparatuses with its/their operating voltage. In this manner the need for a central unit for the voltage supply to the current measuring apparatuses can be obviated, which has a favorable effect on the space requirement in many higher-level applications for the spatially resolved measurement of photons.

Furthermore, the supply bar of the higher-level application now does not need to be configured to withstand large currents and can accordingly be realized by more cost-effective cables. In particular, the individual voltage conditioners also do not need to be configured for a higher power, since in relation to the total number which is provided by the second plurality only a small number of current measuring apparatuses are supplied with voltage in each case. Individual components of a voltage conditioner, such as can be provided in particular by a step-down converter and/or a linear regulator, can thus be constructed in a compact manner in the corresponding rating class that is applicable for the voltage supply of a current measuring apparatus for measuring a photocurrent, such that on the one hand they are of negligible importance in terms of their space requirement. On the other hand, the low additional costs of the plurality of voltage conditioners can be compensated by obviating the need for a central unit for voltage supply, which would be configured for high power and would require corresponding components.

The device preferably comprises at least one scintillator, which, in respect of a preferred direction which during operation of the device corresponds to a direction of incidence of photons to be measured, is arranged upstream of the photoelectric converters. In such cases the scintillator preferably covers all photoelectric converters such that photons coming from the incident direction are absorbed in full by the scintillator. In a scintillator, high-energy photons excite the atoms and/or molecules of the scintillator material by collisions, wherein the excitation energy is emitted again by lower-energy photons. The energy absorbed by the scintillator is preferably negligible compared with the total energy of the high-energy photons absorbed, so that a plurality of lower-energy photons is generated by a high-energy photon by way of the excitations in each case. In particular, the device is configured by the scintillator for the spatially resolved measurement of x-ray photons.

The photoelectric converters are expediently provided in each case by photodiodes. Photodiodes typically have an area in which, for the intensity of the incident light, and thus for the quantity of the incident photons, the intensity is largely proportional to the generated photocurrent. By dimensioning the individually used photodiodes correspondingly and by dosing the intensity of the incident light correspondingly, it is possible for the photodiodes in virtually all typical operating situations to be operated in the linear range, so that not only does a spatially resolved measurement of incident photons take place, but a conclusion regarding the number of photons or the intensity of the incident light in each pixel represented by a photodiode can also be made by way of the photocurrent.

Each of the current measuring apparatuses is expediently provided in each case by a correspondingly configured ASIC. An ASIC is an application-specific integrated circuit, the layout of which has been optimized for a specific application. In this manner it is possible to avoid individual components such as processors or the like, which are originally provided for a multitude of functions, having to be controlled separately. Indeed, as a result an ASIC has one only very reduced cycle of possible executable operations compared with a circuit with a comparable base computing capacity; however, as a result of the integrated functionality and design, the space and energy requirement and the generation of waste heat are significantly lower. Therefore when ASICs are used as current measuring apparatuses, on the one hand it is possible to achieve a particularly compact design of the photoelectric converters and thus a high image resolution. On the other hand, possible impacts from the current measuring apparatus on a temperature-dependent change in the characteristics of the photoelectric converter are better prevented on account of the lower waste heat.

Furthermore, it has proven to be advantageous if the voltage conditioners can be connected in parallel to one another with the supply bar. In this manner it is particularly easy for the same input voltage to be applied to all voltage conditioners in a stable manner, and errors in the voltage regulation of an individual voltage conditioner have no effect or only a negligible effect on other voltage conditioners.

In an advantageous embodiment of the invention, a voltage conditioner comprises a first step-down converter, which is configured to preconvert the supply voltage to a maximum of 0.5 V, preferably a maximum of 300 mV above the operating voltage of a current measuring apparatus. All voltage conditioners preferably comprise in each case a first step-down converter and in particular all voltage conditioners are of the same construction. The operating voltage of a current measuring apparatus includes in particular the voltage at which a current measuring apparatus has to be operated, in order to enable usable measuring results within the desired operation of the apparatus and thus an adequate measurement of the photons.

A step-down converter significantly reduces possible voltage fluctuations in the supply voltage, since a step-down converter is configured by way of the pulse duty factor to provide a constant output voltage in respect of the input voltage at its output and thus fluctuations in an input voltage, which is provided in the present case by the supply voltage, are suppressed. The voltage fluctuations which undergo an absolute reduction can then, if necessary, additionally be stabilized further through fine-tuning.

Furthermore, it has proven to be advantageous if a voltage conditioner has a linear regulator, which is configured to down-convert an input voltage to the operating voltage of a current measuring apparatus and/or to stabilize the same at the operating voltage of a current measuring apparatus. Here the resulting voltage is then preferably the output voltage of the voltage conditioner. In particular, all voltage conditioners have one linear regulator in each case, and all voltage conditioners are preferably of the same construction as one another. The or each linear regulator is preferably configured to down-convert the input voltage with the aid of an auxiliary voltage to the operating voltage of a current measuring apparatus or to stabilize the same at this operating voltage.

Initially in a voltage conditioner the supply voltage is particularly preferably pre-converted to a maximum of 0.5 V, preferably at most 300 mV above the operating voltage of the current measuring apparatus to be supplied by the voltage conditioner, and is then stabilized by the linear regulator at this operating voltage. Larger fluctuations of the supply voltage can thus initially be suppressed by the step-down converter, while the linear regulator is used to subsequently fine-tune the operating voltage.

Here a voltage conditioner expediently comprises a second step-down converter, which is configured to down-convert the supply voltage to an auxiliary voltage of the linear regulator. Here the auxiliary voltage is preferably greater than the input voltage of the linear regulator. Linear voltage regulators, which for regulation purposes in addition to the input voltage operate with an additional auxiliary voltage, which is greater than the input voltage, enable operation with a low voltage excursion, as a result of which power loss can be saved.

At least one embodiment of the invention is directed to an x-ray detector, which comprises an apparatus as described above in at least one embodiment, and a CT with at least one such x-ray detector. The advantages cited for the embodiments of the apparatus and its developments can be applied analogously here to embodiments of the x-ray detector and the CT. In particular in a CT, on account of the technical properties of the rotating assembly, one of the core problems is namely to achieve, with limited available space, as effective a spatially resolved measurement of x-ray photons as possible, which is to have a low power loss and a stable voltage supply.

In FIG. 1 a CT 1 is shown schematically in a cross-sectional view, which has a retaining frame 2 and a rotating assembly 4, which is mounted rotatably in respect of the retaining frame 2 about an axis 6 which is at right angles to the image plane. An energy transmission unit 8 is used to transmit power from a power source 10 arranged on the retaining frame 2 to the consumers, yet to be described, on the rotating assembly 4.

Inter alia an x-ray source 12, a supply bar 14, and an electronics unit 16 are supplied with voltage by the energy transmission unit 8, which transmits a high alternating voltage. For this purpose the high alternating voltage is rectified already in the energy transmission unit 8 in a corresponding rectifier module 18. The individual voltages to the x-ray source 12, the supply bar 14 and the electronics unit 16 are converted again accordingly to the respective intended value. The supply of further components is not shown for the sake of simplicity. In a plurality of parallel branches, the supply bar 14 is for its part connected in a manner still to be described to an apparatus for the spatially resolved measurement of photons, which is provided here by an x-ray detector 20.

During operation a patient's body 22 which is irradiated by x-rays 24 generated in the x-ray source 12 is positioned in the CT 1 along the axis 6. The x-rays 24 penetrate the patient's body 22 and in particular a specific body region to be imaged, and are absorbed here to differing degrees by the penetrated tissue. The intensity of the remaining x-rays 24 is then measured in a spatially resolved manner by the x-ray detector 20, and the measuring results are output for further processing and data transmission to the electronics unit 16.

As a result of the extremely high power consumption of the x-ray source 12 compared with the other consumers on the rotating assembly 4, voltage fluctuations in the x-ray source 12 can manifest as undesirable alternating voltage portions in the said other consumers. This is problematic for a constantly stable detection particularly for the x-ray detector 20 supplied with voltage by way of the supply bar 14, as a result of which the voltage has to be stabilized.

Figure 2:
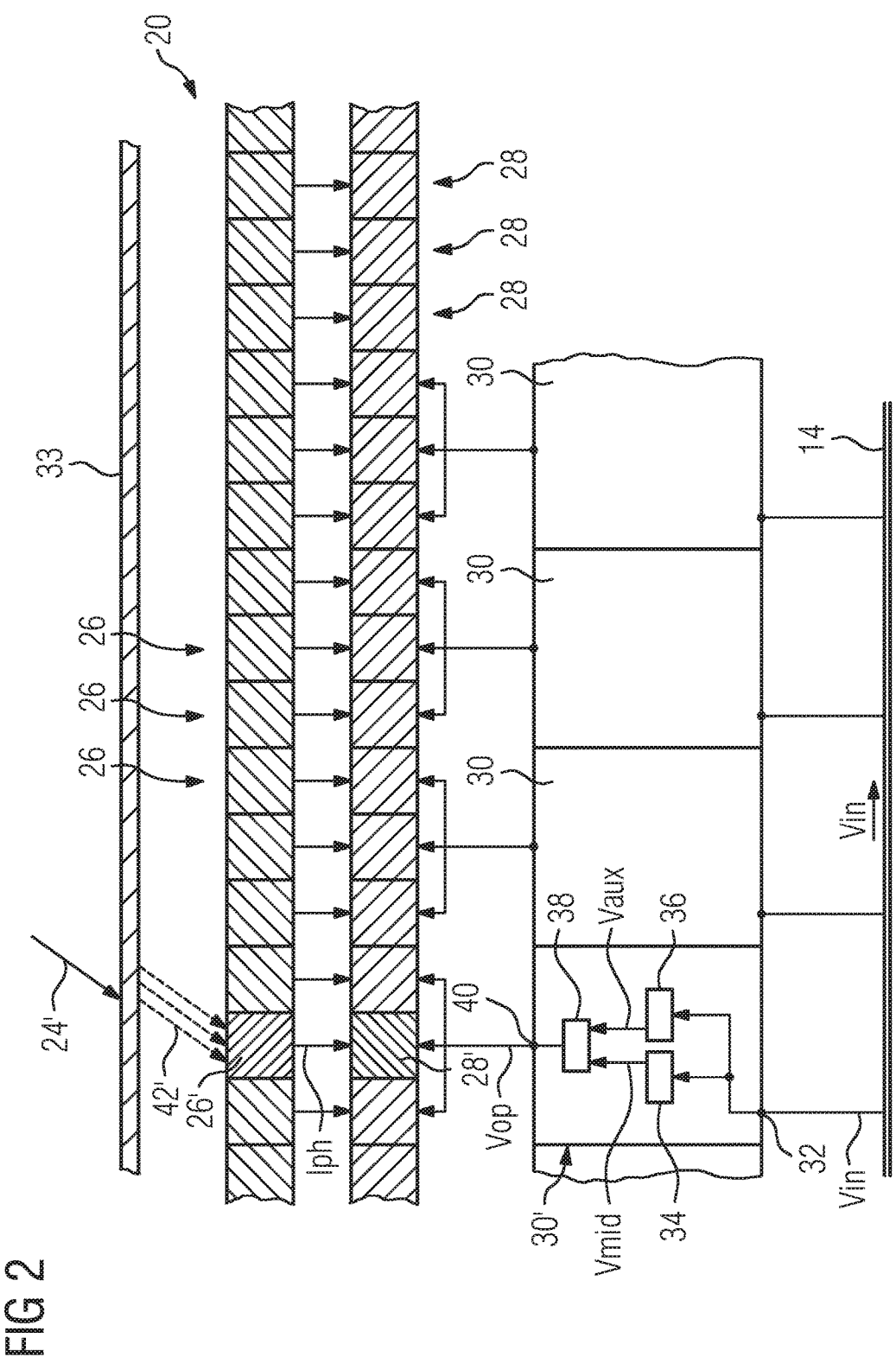
FIG. 2 a block diagram of an x-ray detector according to FIG. 1.

In FIG. 2, a device for the spatially resolved measurement of x-ray photons 24' is shown schematically in a block diagram, and is provided here by an x-ray detector 20 according to FIG. 1. The spatial curvature of the x-ray detector 20 has not been shown here for the sake of simplicity. The x-ray detector 20 has a first plurality of photoelectric converters, which, in the present example embodiment, are each provided by photodiodes 26. Each of the photodiodes 26 is individually connected electrically in each case to a current measuring apparatus for measuring the photocurrent generated as a result of the incidence of light, wherein the current measuring apparatuses are each present here in the form of ASICs 28.

The individual ASICs 28 are each connected in groups to precisely one of the voltage conditioners 30 such that during operation of the x-ray detector 20, each voltage conditioner 30 supplies a small group of ASICs 28 with their respective operating voltage. The voltage conditioners 30 for their part each have terminals 32, at which each individual voltage conditioner 30, all in parallel with one another, are connected to the supply bar 14, by means of which the voltage conditioners 30 obtain their supply voltage Vin in each case. A scintillator 33 is arranged in the beam direction upstream of the photodiodes 26. This generates a plurality of lower-energy photons from few incident x-ray photons 24', which are now detected in a spatially resolved manner by the photodiodes 26.

The inner design of the voltage conditioners 30 which are of the same construction as one another is shown schematically for one voltage conditioner 30'. The terminal 32 is connected in parallel with a first step-down converter 34 and a second step-down converter 36. The supply voltage Vin (to ground, not shown separately) provided by way of the supply bar 14 in the present case has a value of 12V during operation. The first step-down converter 34 pre-converts the supply voltage Vin to an input voltage Vmid of a linear regulator 38, the value of which amounts to approx. 3.6V with a stable supply voltage Vin. The second step-down converter 36 converts the supply voltage Vin to an auxiliary voltage Vaux of approx. 5V.

The input voltage Vmid is now down-converted by the linear regulator 38 with the aid of the auxiliary voltage Vaux to an output value Vop of approx. 3.3V and also stabilized at this value. Here the cited value of Vop is the intended operating voltage of the individual ASICs 28, of which individual groups are connected in parallel in each case with an output 40 of a voltage conditioner 30, and are as a result supplied with the stable operating voltage Vop of 3.3V. When an x-ray photon 24' strikes the scintillator 33, this generates a plurality of low-energy photons 42', which generate a photocurrent Iph in a specific photodiode 26' which is proportional to the intensity of the incident radiation, the low-energy photons 42' being, for example, photons with lower energy than the incident x-ray photons 24' striking the scintillator 33. The photocurrent Iph is then measured in the ASIC 28' connected to the photodiode 26'. For this purpose the ASIC is supplied with its operating voltage Vop by the voltage conditioner 30'.

Fluctuations in the supply voltage Vin, which may be caused by brief output peaks in the consumption of the x-ray source 12 for instance, may thus firstly be significantly reduced in the respective voltage conditioner 30 by the first step-down converter 34 and then suppressed by the linear regulator 38 to a degree which is insignificant to the operation of the ASICs 28. The stable operating voltage Vop of the ASICs can ensure that the measured photocurrents Iph of the photodiodes 26 also have a fixed proportionality over time in relation to the intensity of the incident x-rays 24.

Furthermore, the use of the decentralized, local voltage conditioners 30, which in each case only supply individual ASICs 28 or small groups of ASICs 28 with the operating voltage Vop, has the advantage that on the one hand the need for a central unit for voltage conditioning for all ASICs is obviated, as a result of which significant space can be saved in the rotating assembly. The individual components of the voltage conditioners 30, 30', in particular the step-down converters 34, 36, can be chosen to have very small dimensions in view of their merely low power consumption. Moreover, no heavy cables which are designed to carry large currents have to be guided from a central unit for the voltage supply to the individual ASICs, since a voltage drop which fluctuates with the current is well controlled by the step-down converters 34, 36.

Although the invention has been illustrated and described in more detail by the preferred example embodiment, the invention is not restricted by this example embodiment. Other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A device for spatially resolved measurement of photons, comprising:
   a plurality of photoelectric converters;
   a plurality of current measuring apparatuses; and
   a plurality of voltage conditioners,
   wherein each current measuring apparatus, of the plurality of current measuring apparatuses, is electrically connected to at least one photoelectric converter of the plurality of photoelectric converters,
   wherein each voltage conditioner, of the plurality of voltage conditioners, is electrically connected to at least one current measuring apparatus of the plurality of current measuring apparatuses,
   wherein each photoelectric converter of the plurality of photoelectric converters is configured to generate a photocurrent from an incident photon,
   wherein each voltage conditioner is connectable to a supply bar, configured to provide a supply voltage, and wherein each of the voltage conditioners is configured to down-convert the supply voltage to an operating voltage of one of the plurality of current measuring apparatuses,
   wherein each current measuring apparatus is configured to measure a photocurrent under operating voltage, when the photocurrent is generated in respective one of the plurality of photoelectric converters electrically connected to the respective current measuring apparatus, and
   wherein a voltage conditioner, of the plurality of voltage conditioners, includes a first step-down converter, configured to pre-convert the supply voltage to a maximum of 0.5 V above the operating voltage of a current measuring apparatus, of the plurality of current measuring apparatuses.

2. The device of claim 1, further comprising:
   at least one scintillator, arranged upstream of the plurality of photoelectric converters with respect of a direction which, during operation of the device, corresponds to a direction of incidence of photons to be measured.

3. The device of claim 2, wherein each of the plurality of photoelectric converters are provided by photodiodes.

4. The device of claim 2, wherein each of the plurality of current measuring apparatuses is provided by a correspondingly configured ASIC.

5. The device of claim 2, wherein the plurality of voltage conditioners are connectable, in parallel with one another, to the supply bar.

6. The device of claim 2, wherein a voltage conditioner, of the plurality of voltage conditioners, includes a linear regulator, configured to at least one of
   down-convert an input voltage to the operating voltage of a current measuring apparatus, of the plurality of current measuring apparatuses and
   stabilize the input voltage at the operating voltage of a current measuring apparatus, of the plurality of current measuring apparatuses.

7. The device of claim 6, wherein a voltage conditioner, of the plurality of voltage conditioners, comprises a second step-down converter, configured to down-convert the supply voltage to an auxiliary voltage of the linear regulator.

8. An x-ray detector comprising the device of claim 2.

9. A computed tomograph including at least one x-ray detector as claimed in claim 8.

10. The device of claim 1, wherein each of the plurality of photoelectric converters are provided by photodiodes.

11. The device of claim 1, wherein each of the plurality of current measuring apparatuses is provided by a correspondingly configured ASIC.

12. The device of claim 1, wherein the plurality of voltage conditioners are connectable, in parallel with one another, to the supply bar.

13. The device of claim 1, wherein a voltage conditioner, of the plurality of voltage conditioners, includes a linear regulator, configured to at least one of
   down-convert an input voltage to the operating voltage of a current measuring apparatus, of the plurality of current measuring apparatuses and
   stabilize the input voltage at the operating voltage of a current measuring apparatus, of the plurality of current measuring apparatuses.

14. The device of claim 13, wherein a voltage conditioner, of the plurality of voltage conditioners, comprises a second step-down converter, configured to down-convert the supply voltage to an auxiliary voltage of the linear regulator.

15. An x-ray detector comprising the device of claim 1.

16. A computed tomograph including at least one x-ray detector as claimed in claim 15.

17. The device of claim 1, wherein the device is for spatially resolved measurement of x-ray photons.

* * * * *